(12) United States Patent
Ma et al.

(10) Patent No.: US 9,682,870 B2
(45) Date of Patent: Jun. 20, 2017

(54) METHOD OF SYNTHESIZING FERRATE

(71) Applicant: Harbin Institute of Technology, Harbin, Heilongjiang (CN)

(72) Inventors: Jun Ma, Harbin (CN); Yulei Liu, Harbin (CN); Xiaodan Zhao, Harbin (CN); Jiayue Xiao, Harbin (CN)

(*) Notice: Subject to any disclaimer, the term of this patent is extended or adjusted under 35 U.S.C. 154(b) by 68 days.

(21) Appl. No.: 14/687,828

(22) Filed: Apr. 15, 2015

(65) Prior Publication Data

US 2016/0304356 A1    Oct. 20, 2016

(51) Int. Cl.
*C01G 49/00*    (2006.01)
*A61K 33/26*    (2006.01)

(52) U.S. Cl.
CPC .......... *C01G 49/0081* (2013.01); *A61K 33/26* (2013.01)

(58) Field of Classification Search
CPC ....... C02F 1/72; C02F 1/5236; C01G 49/0081
USPC .................. 423/594.1, 594.2, 140, 142, 143; 424/646
See application file for complete search history.

(56) References Cited

U.S. PATENT DOCUMENTS 5,202,108 A * 4/1993 Deininger .......... C01G 49/0081
423/266
2007/0217954 A1* 9/2007 Powell ................ B01F 13/1055
422/82.09

FOREIGN PATENT DOCUMENTS

WO    2012/044358    * 4/2012

OTHER PUBLICATIONS

Zhang, et al., "Influence of impurities on stability of composite ferrate solution", Journal of Harbin Institute of Technology, vol. 40, No. 2, Feb. 2008, pp. 217-219.*
Translation of Zhang, et al.,"Influence of impurities on stability of composite ferrate solution", Journal of Harbin Institute of Technology, vol. 40, No. 2, Feb. 2008, pp. 217-219.*

* cited by examiner

*Primary Examiner* — Steven Bos
(74) *Attorney, Agent, or Firm* — Novoclaims Patent Services LLC; Mei Lin Wong

(57) ABSTRACT

A method of synthesizing ferrate, which includes the steps of: (a) weighing and obtaining iron salts, activating agents, alkalinizing agents and oxidizing agents solution; (b) mixing uniformly the iron salts, the activating agents and the alkalinizing agents, heating to 30~398° C. and maintaining for 1 min~60 min to obtain a mixture; (c) adding the oxidizing agents solution to the mixture with an adding time of less than 10 minutes, then obtaining a precursor; and (d) natural cooling the precursor, then mixing the precursor with water and stirring evenly to obtain a final product of ferrate, wherein a volume ratio of the precursor and the water is 1:1~5. The method involves low power consumption, low temperature, low explosion risk, non-complicated steps and procedures, short synthetic time and high ferrate conversion efficiency. The method produces ferrate of high yield and good stability, and is suitable for producing ferrate composite pharmaceuticals in industrialized mass production.

20 Claims, 1 Drawing Sheet

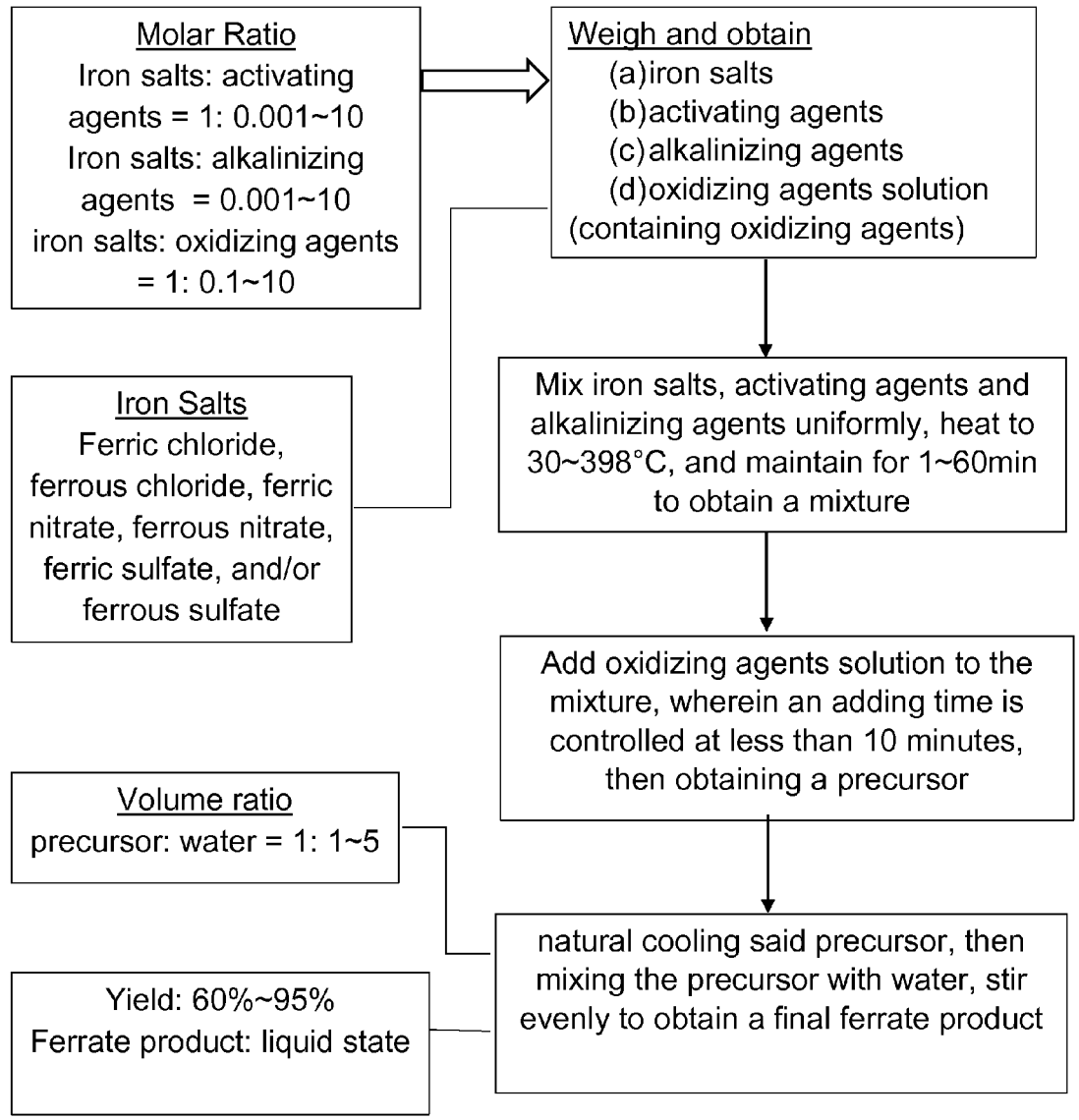

METHOD OF SYNTHESIZING FERRATE

BACKGROUND OF THE PRESENT INVENTION

Field of Invention

The present invention relates to a method of synthesizing ferrate, and more particularly to a method of producing ferrate composite pharmaceutical which is suitable for mass production and industrialization with high quality such that the application of ferrate can be fully realized.

Description of Related Arts

At present, there are three basic methods for synthesizing ferrate: (1) wet oxidation; (2) electrolysis; (3) high temperature peroxidation (dry). However, all these methods have a certain level of limitation in industrial production. The method of hypochlorite oxidation is mature, and the yield and purity is good. However, during the operation, the temperature is required to keep at near zero degrees Celsius, the operation is complicated and susceptible to introduction of other contaminants. The method of electrolysis is simple in operation while the raw materials consumption is low. However, the power consumption is high, the number of by-products is high, the number of influencing factors is high and the yield is low. The method of high temperature peroxidation has a higher yield and purity. However, a higher temperature is required, which results in the risk of explosion.

Since ferrate treatment results in multifunctional water purification effect such as oxidation, adsorption, co-precipitation, disinfection, sterilization and algae removal, it is an ideal water treatment agent for industrial wastewater and drinking water. At present, the limitations of large scale application and use of ferrate include high complexity of its synthetic methods, low yield, large commercial investment requirement, and high production cost.

In Russ J Inorg Chem, 34 (1989), pp. 1250-1253, Y. M. Kiselev et al. disclosed a method of preparing ferrate by heating iron oxide and sodium peroxide at 370° C. while introducing oxygen gas. This method is very difficult in operation and there is a danger of explosion. In "Preparation and purification of potassium ferrate(VI)" Chem Anal, 73 (1951), pp. 1379-1381, G. W. Thompson et al. disclosed a method of preparing ferrate by using alkaline sodium hypochlorite and ferric nitrate, and the ferrate product in solid state is precipitated by saturated potassium hydroxide. In this method, during the reaction, the temperature is controlled to not exceeding 20° C., and purification by organic substances such as benzene, ethanol and ethyl ether is required. In U.S. Pat. No. 5,746,994, the method of preparing ferrate by oxidizing ferric sulfate with monoperoxosulfate in the presence of a strong base is disclosed. This method requires an ice bath and the reaction temperature is required to be controlled below 0° C. In the PCT publication number WO2012/044358 A1, which is published on Aug. 7, 2013, Virende K. Sharma disclosed a method of preparing a ferrate solution by first obtaining a ferrate intermediate through heating ferric salts and sodium peroxide under 400~650° C., through an electrochemical process, and/or through burning a mixture of iron salts and ethylene glycol then, after cooling, adding a halogen solution or introducing ozone to the ferrate intermediate. This method is very complicated, requires high temperature heating or high power input, which has a high power consumption. In the Canadian patent number CA2703708C, published on Jan. 31, 2012, Lee Edward Ciampi et al. disclosed an electrochemical synthetic process for producing ferrate continuously by utilizing a two-reaction chamber and two-electrode system. The efficiency of this method is affected by many factors which includes the electrode materials, composition of the electrolytes and current density while there exists the problem of electrode purification. In recent years, domestic scholars in our country are increasingly concerned about the application of ferrate in contaminant removal from drinking water. However, due to the lack of experience and reference of mature synthetic technology, the implementation of commercial production of ferrate is not realized.

SUMMARY OF THE PRESENT INVENTION

In order to solve the problem of ferrate production which includes high power consumption, low yield and poor stability of ferrate products, an object of the present invention is to provide a method of producing ferrate which is suitable for large scale production.

Another object of the present invention is to provide a method of synthesizing ferrate which is suitable for large scale production, wherein the method involves low power consumption, lenient temperature requirement, low risk of explosion, non-complicated steps and procedures, short synthetic time, high ferrate conversion efficiency and produces ferrate products with high yield and excellence stability.

Another object of the present invention is to provide a method of synthesizing ferrate which is used as a pharmaceutical composition.

Another object of the present invention is to provide a method of synthesizing ferrate which produces ferrate in liquid form in such a manner that the ferrate is available for immediate use without further processing steps or procedures.

Another object of the present invention is to provide a method of synthesizing ferrate which produces ferrate in liquid form of high yield and high purity such that the ferrate is available for immediate use without further purification or precipitation steps or procedures.

Additional advantages and features of the invention will become apparent from the description which follows, and may be realized by means of the instrumentalities and combinations particular point out in the appended claims.

According to the preferred embodiment of the present invention, the foregoing and other objects and advantages are attained by a method of synthesizing ferrate for ferrate composite pharmaceutical production, comprising the steps of:

(a) Weight to obtain iron salts, activating agents, alkalinizing agents and oxidizing agents solution, where the molar ratio of iron salts and activating agents is 1:0.001~10, the molar ratio of iron salts and alkalinizing agents is 1:2~20, the molar ratio of iron salts and oxidizing agents in the oxidizing agents solution is 1:0.1~10;

(b) Mixing the iron salts, the activating agents and the alkalinizing agents, heating the iron salts, the activating agents and the alkalinizing agents to a temperature of 30~398° C. and maintaining the iron salts, the activating agents and the alkalinizing agents for 1 min~60 min to obtain a mixture;

(c) Adding the oxidizing agents solution to the mixture, the adding time is controlled at less than 10 minutes, and obtaining a precursor; and (d) Natural cooling the precursor, then mixing the precursor with water and stirring to obtain a ferrate composite pharmaceutical, where the ratio of the precursor and the water by volume is 1:1~5.

In the above process, if the iron salt is a composition, the ratio of different ingredients is any ratio; if the activating agent is a composition, the ratio of its ingredients is any ratio; if the alkalinizing agent is a composition, the ratio of its ingredients is any ratio; if the oxidizing agent is a composition, the ratio of its ingredients is any ratio.

In the step (b), if the alkalinizing agent is sodium carbonate, sodium bicarbonate, potassium bicarbonate or potassium carbonate, the ferrate being produced is bright purple in color; if the alkalinizing agent is sodium hydroxide or potassium hydroxide, the ferrate being produced is gray purple in color.

In the step (b), if the temperature is 30~150° C., the addition of activating agent can increase the conversion efficiency of ferrate by 20~40%; if the temperature is 151~398° C., the addition of activating agent can increase the conversion efficiency of ferrate by 10~20%; where the activating agent refers to the activating agent in step (a).

Advantageous Effect

The present invention provides a process of producing ferrate in ferrate composite pharmaceutical production. First, the present invention combines the process of heating and the process of adding oxidizing agent solution to achieve a suitable heating temperature, therefore the operating process is safe and fast. Second, the present invention is capable maintaining an alkaline environment for the process of producing ferrate with a strong base and a weak acid, that the amount of base is reduced and the production cost is lowered. In addition, the ferrate solution being produced does not require any pH adjustment and can be applied directly for treatment of drinking water, wastewater, sludge and gas. On the other hand, the ferrate produced by the method of the present invention is existed in liquid state, which is relatively more stable, therefore the process of purification and solidification can be omitted and the production process is greatly simplified, or the ferrate produced by the method of the present invention can be produced and used simultaneously. According to the method of the present invention, the yield of ferrate can reach 60~95%. The maximum absorption peak of UV-Visible spectrum is 525 nm.

The present invention is used for preparing a ferrate composite pharmaceutical.

BRIEF DESCRIPTION OF THE DRAWINGS

FIG. 1 is a flow chart illustration of a process of synthesizing ferrate according to the preferred embodiment of the present invention.

DETAILED DESCRIPTION OF THE PREFERRED EMBODIMENT

The present invention is further described in details with the accompanying drawings and embodiments. The following embodiments are shown and described for the purposes of illustrating the functional and structural principles of the present invention and is subject to change without departure from such principles. Therefore, this invention includes all modifications encompassed within the spirit and scope of the present invention.

Embodiment 1

According to a method of synthesizing ferrate composite pharmaceutical of the preferred embodiment of the present invention, the process comprises the following steps:

(a) Weight to obtain iron salts, activating agents, alkalinizing agents and oxidizing agents solution, where the molar ratio of iron salts and activating agents is 1:0.001~10, the molar ratio of iron salts and alkalinizing agents is 1:2~20, the molar ratio of iron salts and oxidizing agents in the oxidizing agents solution is 1:0.1~10;

(b) Mixing the iron salts, the activating agents and the alkalinizing agents, heating the iron salts, the activating agents and the alkalinizing agents to a temperature of 30~398° C. and maintaining the iron salts, the activating agents and alkalinizing agents for a time of 1 min~60 min to obtain a mixture;

(c) Adding the oxidizing agents solution to the mixture in which an adding time is controlled at less than 10 minutes, and obtaining a precursor; and (d) Natural cooling the precursor, then mixing the precursor with water and stirring to obtain ferrate products, which is used as a ferrate composite pharmaceutical, where the volume ratio of the precursor and the water is 1:1~5.

It is worth mentioning that the ferrate composite pharmaceutical produced by the method of the present invention can also be used for other purposes, such as drinking water treatment, wastewater treatment and etc.

Preferably, in the step (d), the process of natural cooling is cooling to room temperature.

Embodiment 2

According to a method of synthesizing ferrate of this preferred embodiment of the present invention, all the steps and parameters are the same as that of embodiment 1 except the followings: in step (a), the iron salts refer to a composition containing one or more of: ferric chloride, ferrous chloride, ferric nitrate, ferrous nitrate, ferric sulfate and ferrous sulfate.

Embodiment 3

According to a method of synthesizing ferrate of this preferred embodiment of the present invention, all the steps and parameters are the same as that of embodiment 1 except the followings: in step (a), the activating agents refers to one or more of: potassium permanganate, potassium dichromate, potassium chlorate, persulfate and monopersulfates.

Embodiment 4

According to a method of synthesizing ferrate of this preferred embodiment of the present invention, all the steps and parameters are the same as that of embodiment 1 except the followings: in step (a), the alkalinizing agents refers to one or more of: sodium hydroxide, sodium carbonate, sodium bicarbonate, potassium hydroxide, potassium bicarbonate and potassium carbonate.

Embodiment 5

According to a method of synthesizing ferrate of this preferred embodiment of the present invention, all the steps and parameters are the same as that of embodiment 1 except the followings: in step (a), the oxidizing agents in the oxidizing solution refers to one or more of: potassium permanganate, potassium dichromate, hydrogen peroxide, ozone, sodium hypochlorite, potassium hypochlorite, potassium chlorate, perchlorate, persulfate and monopersulfate. The concentration of the oxidizing agents solution is 0.1 mol/L~3 mol/L.

Embodiment 6

According to a method of synthesizing ferrate of this preferred embodiment of the present invention, all the steps and parameters are the same as that of embodiments 1-5 except the followings: in step (a), the concentration of the oxidizing agents solution is 1.5 mol/L.

Embodiment 7

According to a method of synthesizing ferrate of this preferred embodiment of the present invention, all the steps and parameters are the same as that of embodiment 1 except the followings: in step (b), the temperature is 31° C.~150° C.

Embodiment 8

According to a method of synthesizing ferrate of this preferred embodiment of the present invention, all the steps and parameters are the same as that of embodiment 1 except the followings: in step (b), the temperature is 151° C.~397° C.

Embodiment 9

According to a method of synthesizing ferrate of this preferred embodiment of the present invention, all the steps and parameters are the same as that of embodiment 1 except the followings: in step (b), the time is 8 min~10 min.

Embodiment 10

According to a method of synthesizing ferrate of this preferred embodiment of the present invention, all the steps and parameters are the same as that of embodiment 1 except the followings: in step (b), the time is 25 min~30 min.

The advantageous effect of the method of synthesizing ferrate of the present invention is tested and verified by the followings:

Embodiment 1

According to a method of synthesizing ferrate composite pharmaceutical of this preferred embodiment of the present invention, the method comprises the following steps:

(a) Weight to obtain 2.5 g of ferric nitrate, 0.5 g of potassium dichromate, 2.2 g of potassium hydroxide and 5 mL of 1.5 mol/L hydrogen peroxide solution;

(b) Mixing the ferric nitrate, the potassium dichromate and the potassium hydroxide, heating the ferric nitrate, the potassium dichromate and the potassium hydroxide to a temperature of 300° C. and maintaining the ferric nitrate, the potassium dichromate and the potassium hydroxide for a time of 5 min to obtain a mixture;

(c) Adding the 5 mL of hydrogen peroxide solution (1.5 mol/L) to the mixture in which an adding time is controlled at less than 0.5 minute, and obtaining a precursor; and (d) Natural cooling the precursor obtained, then mixing the precursor with 5 mL of water and stirring to obtain ferrate products, which is a ferrate composite pharmaceutical, where a yield of the ferrate products is 73~75%.

Embodiment 2

According to a method of synthesizing ferrate composite pharmaceutical of this preferred embodiment of the present invention, the method comprises the following steps:

(a) Weight to obtain 2.0 g of ferric sulfate, 0.5 g of activating agent, 2.2 g of potassium hydroxide and 3 mL of 3 mol/L hydrogen peroxide solution, where the activating agent is a mixture of potassium persulfate and potassium permanganate of which the mass ratio of potassium persulfate and potassium permanganate is 4:1;

(b) Mixing the ferric sulfate, the activating agent and the potassium hydroxide, heating the ferric sulfate, the activating agent and the potassium hydroxide to a temperature of 200° C. and maintaining for a time of 7.5 min to obtain a mixture;

(c) Adding the 3 mL of hydrogen peroxide solution (3 mol/L) to the mixture in which an adding time is controlled at less than 0.5 minute, and obtaining a precursor; and (d) Natural cooling the precursor, then mixing the precursor with 5 mL of water and stirring to obtain ferrate products, which is a ferrate composite pharmaceutical, where a yield of the ferrate products is 90~93%.

Embodiment 3

According to a method of synthesizing ferrate composite pharmaceutical of this preferred embodiment of the present invention, the method comprises the following steps:

(a) Weight to obtain 2.5 g of ferric nitrate, 0.5 g of activating agent, 2.2 g of potassium hydroxide and 5 mL of 2 mol/L sodium hypochlorite solution; where the activating agent is a mixture of potassium dichromate and potassium chlorate of which the mass ratio of potassium dichromate and potassium chlorate is 3:2;

(b) Mixing the ferric nitrate, the activating agent and the potassium hydroxide obtained, heating the ferric nitrate, the activating agent and the potassium hydroxide to a temperature of 150° C. and maintaining the ferric nitrate, the activating agent and the potassium hydroxide for a time of 10 min to obtain a mixture;

(c) Adding the 5 mL of sodium hypochlorite solution (2 mol/L) to the mixture in which an adding time is controlled at less than 0.5 minute, and obtaining a precursor; and (d) Natural cooling the precursor, then mixing the precursor with 5 mL of water and stirring to obtain ferrate products, which is a ferrate composite pharmaceutical, where a yield of the ferrate products is 83~86%.

Embodiment 4

According to a method of synthesizing ferrate composite pharmaceutical of this preferred embodiment of the present invention, the method comprises the following steps:

(a) Weight to obtain 2.5 g of ferric nitrate, 0.5 g of activating agent, 2.2 g of potassium hydroxide and 5 mL of 1.5 mol/L perchloric acid solution, where the activating agent is a mixture of potassium dichromate and peroxydisulfates of which the mass ratio of potassium dichromate and peroxydisulfates is 2:3;

(b) Mixing the ferric nitrate, the activating agent and the potassium hydroxide, heating the ferric nitrate, the activating agent and the potassium hydroxide to a temperature of 350° C. and maintaining the ferric nitrate, the activating agent and the potassium hydroxide for a time of 5 min to obtain a mixture;

(c) Adding the 5 mL of perchloric acid solution (1.5 mol/L) to the mixture in which an adding time is controlled at less than 2 minute, and obtaining a precursor; and (d) Natural cooling the precursor, then mixing the precursor with 5 mL of water and stirring to obtain ferrate products, which is a ferrate composite pharmaceutical, where a yield of the ferrate products is 90~93%.

Embodiment 5

According to a method of synthesizing ferrate composite pharmaceutical of this preferred embodiment of the present invention, the method comprises the following steps:

(a) Weight to obtain 2.5 g of ferric nitrate, 0.5 g of activating agent, 2.2 g of potassium hydroxide and 5 mL of 0.1 mol/L ozone solution, where the activating agent is a mixture of potassium dichromate and monopersulfate of which the mass ratio of potassium dichromate and monopersulfate is 1:4;

(b) Mixing the ferric nitrate, the activating agent and the potassium hydroxide, heating the ferric nitrate, the activating agent and the potassium hydroxide to a temperature of 40° C. and maintaining the ferric nitrate, the activating agent and the potassium hydroxide for a time of 5 min to obtain a mixture;

(c) Adding the 5 mL of ozone solution (0.1 mol/L) to the mixture in which an adding time is controlled at less than 0.5 minute, and obtaining a precursor; and (d) Natural cooling the precursor, then mixing the precursor with 5 mL of water and stirring to obtain ferrate products, which is a ferrate composite pharmaceutical, where a yield of the ferrate products is 86~90%.

Embodiment 6

According to a method of synthesizing ferrate composite pharmaceutical of this preferred embodiment of the present invention, the method comprises the following steps:

(a) Weight to obtain 2.5 g of ferric chloride, 0.5 g of potassium permanganate, 2.2 g of potassium hydroxide and 5 mL of 2 mol/L potassium hypochlorite solution;

(b) Mixing the ferric chloride, the potassium permanganate and the potassium hydroxide, heating the ferric chloride, the potassium permanganate and the potassium hydroxide to a temperature of 300° C. and maintaining the ferric chloride, the potassium permanganate and the potassium hydroxide for a time of 5 min to obtain a mixture;

(c) Adding the 5 mL of potassium hypochlorite solution (2 mol/L) to the mixture in which an adding time is controlled at less than 1 minute, and obtaining a precursor; and (d) Natural cooling the precursor, then mixing the precursor with 10 mL of water and stirring to obtain ferrate products, which is a ferrate composite pharmaceutical, where a yield of the ferrate products is 91~93%.

According to a method of synthesizing ferrate composite pharmaceutical of this preferred embodiment of the present invention, the method comprises the following steps:

(a) Weight to obtain 2.5 g of ferric chloride, 0.5 g of potassium dichromate, 2.2 g of potassium hydroxide and 5 mL of 1.5 mol/L hydrogen peroxide solution;

(b) Mixing the ferric chloride, the potassium dichromate and the potassium hydroxide, heating the ferric chloride, the potassium dichromate and the potassium hydroxide to a temperature of 200° C. and maintaining the ferric chloride, the potassium dichromate and the potassium hydroxide for a time of 15 min to obtain a mixture;

(c) Adding the 5 mL of hydrogen peroxide solution (1.5 mol/L) to the mixture in which an adding time is controlled at less than 0.5 minute, and obtaining a precursor; and (d) Natural cooling the precursor, then mixing the precursor with 5 mL of water and stirring to obtain ferrate products, which is a ferrate composite pharmaceutical, where a yield of the ferrate products is 82~84%.

Embodiment 8

According to a method of synthesizing ferrate composite pharmaceutical of this preferred embodiment of the present invention, the method comprises the following steps:

(a) Weight to obtain 2.5 g of ferric chloride, 0.5 g of potassium dichromate, 2.2 g of sodium carbonate and 5 mL of 1.5 mol/L potassium persulfate solution;

(b) Mixing the ferric chloride, the potassium dichromate and the sodium carbonate, heating the ferric chloride, the potassium dichromate and the sodium carbonate to a temperature of 200° C. and maintaining the ferric chloride, the potassium dichromate and the sodium carbonate for a time of 9 min to obtain a mixture;

(c) Adding the 5 mL of potassium persulfate solution (1.5 mol/L) to the mixture in which an adding time is controlled at less than 2 minute, and obtaining a precursor; and (d) Natural cooling the precursor, then mixing the precursor with 5 mL of water and stirring to obtain ferrate products, which is a ferrate composite pharmaceutical, where a yield of the ferrate products is 89~93%.

Embodiment 9

According to a method of synthesizing ferrate composite pharmaceutical of this preferred embodiment of the present invention, the method comprises the following steps:

(a) Weight to obtain 2.5 g of ferric nitrate, 0.5 g of potassium dichromate, 2.2 g of potassium hydroxide and 5 mL of 1.5 mol/L hydrogen peroxide solution;

(b) Mixing the ferric nitrate, the potassium dichromate and the potassium hydroxide, heating the ferric nitrate, the potassium dichromate and the potassium hydroxide to a temperature of 390° C. and maintaining the ferric nitrate, the potassium dichromate and the potassium hydroxide for a time of 20 min to obtain a mixture;

(c) Adding the 5 mL of hydrogen peroxide solution (1.5 mol/L) to the mixture in which an adding time is controlled at less than 5 minute, and obtaining a precursor; and (d) Natural cooling the precursor, then mixing the precursor with 5 mL of water and stirring to obtain ferrate products, which is a ferrate composite pharmaceutical, where a yield of the ferrate products is 73~78%.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of synthesizing ferrate composite pharmaceuticals, comprising the steps of:
  (a) weighing iron salts, activating agents, alkalinizing agents and oxidizing agents solution to obtain a molar ratio of iron salts and activating agents of 1:0.001~10, a molar ratio of iron salts and alkalinizing agents of 1:2~20, a molar ratio of iron salts and oxidizing agents in the oxidizing agents solution of 1:0.1~10;

(b) mixing said iron salts, said activating agents and said alkalinizing agents, then heating said iron salts, said activating agents and said alkalinizing agents after mixing to a temperature of 30° C.~398° C. and maintaining said iron salts, said activating agents and said alkalinizing agents after heating for a time of 1 min~60 min to obtain a mixture;

(c) adding said oxidizing agents solution to said mixture for an adding time controlled at less than 10 minutes to obtain a precursor; and (d) natural cooling said precursor, then mixing said precursor with water and stirring to obtain a final product of ferrate composite pharmaceuticals, wherein a volume ratio of said precursor and said water is 1:1~5.

2. The method of synthesizing ferrate composite pharmaceuticals according to claim 1, wherein said iron salts in the step (a) is one or more selected from the group consisting of: ferric chloride, ferrous chloride, ferric nitrate, ferrous nitrate, ferric sulfate and ferrous sulfate.

3. The method of synthesizing ferrate composite pharmaceuticals according to claim 1, wherein said activating agents in the step (a) is one or more selected from the group consisting of: potassium permanganate, potassium dichromate, potassium chlorate, persulfate and monopersulfate.

4. The method of synthesizing ferrate composite pharmaceuticals according to claim 1, wherein said alkalinizing agents in the step (a) is one or more selected from the group consisting of: sodium hydroxide, sodium carbonate, sodium bicarbonate, potassium hydroxide, potassium bicarbonate and potassium carbonate.

5. The method of synthesizing ferrate composite pharmaceuticals according to claim 1, wherein said oxidizing agents solution in the step (a) is one or more selected from the group consisting of: potassium permanganate, potassium dichromate, hydrogen peroxide, ozone, sodium hypochlorite, potassium hypochlorite, potassium chlorate, perchlorate, persulfate and monopersulfate, wherein a concentration of said oxidizing agents solution is 0.1 mol/L~3 mol/L.

6. The method of synthesizing ferrate composite pharmaceuticals according to claim 5, wherein said concentration of said oxidizing agents solution is 1.5 mol/L.

7. The method of synthesizing ferrate composite pharmaceuticals according to claim 1, wherein in the step (b), said temperature is 31° C.~150° C.

8. The method of synthesizing ferrate composite pharmaceuticals according to claim 1, wherein in the step (b), said temperature is 151° C.~397° C.

9. The method of synthesizing ferrate composite pharmaceuticals according to claim 1, wherein in the step (b), said time is 8 min~10 min.

10. The method of synthesizing ferrate composite pharmaceuticals according to claim 1, wherein in the step (b), said time is 25 min~30 min.

11. A method of synthesizing ferrate for producing ferrate composite pharmaceuticals in industrialized mass production, comprising the steps of:

(a) weighing iron salts, activating agents, alkalinizing agents and oxidizing agents solution to obtain a molar ratio of iron salts and activating agents of 1:0.001~10, a molar ratio of iron salts and alkalinizing agents of 1:2~20, a molar ratio of iron salts and oxidizing agents in the oxidizing agents solution of 1:0.1~10;

(b) mixing said iron salts, said activating agents and said alkalinizing agents and then heating said iron salts, said activating agents and said alkalinizing agents after mixing to a temperature of 30° C.~398° C.;

(c) then maintaining said iron salts, said activating agents and said alkalinizing agents after the step (b) for a time of 1 min~60 min to obtain a mixture;

(d) adding said oxidizing agents solution to said mixture for an adding time controlled at less than 10 minutes to obtain a precursor; and (e) natural cooling said precursor, then mixing said precursor with water and stirring to obtain a final product of ferrate, wherein a volume ratio of said precursor and said water is 1:1~5, wherein a temperature for said method is between 30° C. and 398° C. and a processing time for said method is controlled to approximately less than 120 minutes, wherein a yield of said final product of ferrate is 60%~95% and the maximum absorption peak in UV-Visible spectrum of said final product of ferrate is 525 nm, wherein said final product of ferrate is in liquid state.

12. The method of synthesizing ferrate for producing ferrate composite pharmaceuticals according to claim 11, wherein said iron salts in the step (a) is one or more selected from the group consisting of: ferric chloride, ferrous chloride, ferric nitrate, ferrous nitrate, ferric sulfate and ferrous sulfate.

13. The method of synthesizing ferrate for producing ferrate composite pharmaceuticals according to claim 12, wherein said activating agents in the step (a) is one or more selected from the group consisting of: potassium permanganate, potassium dichromate, potassium chlorate, persulfate and monopersulfate, said alkalinizing agents in the step (a) is one or more selected from the group consisting of: sodium hydroxide, sodium carbonate, sodium bicarbonate, potassium hydroxide, potassium bicarbonate and potassium carbonate, said oxidizing agents solution in the step (a) is one or more selected from the group consisting of: potassium permanganate, potassium dichromate, hydrogen peroxide, ozone, sodium hypochlorite, potassium hypochlorite, potassium chlorate, perchlorate, persulfate and monopersulfate, wherein a concentration of said oxidizing agents solution is 0.1 mol/L~3 mol/L.

14. The method of synthesizing ferrate for producing ferrate composite pharmaceuticals according to claim 12, wherein in the step (b), said temperature is 31° C.~150° C., wherein after the step (b), further comprises the step of: adding an additional amount of activating agents so as to increase a conversion efficiency of ferrate by 20%~40%.

15. The method of synthesizing ferrate for producing ferrate composite pharmaceuticals according to claim 13, wherein in the step (b), said temperature is 31° C.~150° C., wherein after the step (b), further comprises the step of: adding an additional amount of activating agents so as to increase a conversion efficiency of ferrate by 20%~40%.

16. The method of synthesizing ferrate for producing ferrate composite pharmaceuticals according to claim 13, wherein in the step (b), said temperature is 151° C.~397° C., wherein after the step (b), further comprises the step of: adding an additional amount of activating agents so as to increase a conversion efficiency of ferrate by 10%~20%.

17. The method of synthesizing ferrate for producing ferrate composite pharmaceuticals according to claim 15, wherein in the step (c), said time is 8 min~10 min, wherein said processing time for said method is approximately less than 60 minutes.

18. The method of synthesizing ferrate for producing ferrate composite pharmaceuticals according to claim 16, wherein in the step (c), said time is 8 min~10 min, wherein said processing time for said method is approximately less than 60 minutes.

19. The method of synthesizing ferrate for producing ferrate composite pharmaceuticals according to claim 11, wherein in the step (a), said iron salts is ferrate nitrate, said activating agents is potassium dichromate and monopersulfate with a mass ratio of 1:4, said alkalinizing agents is potassium hydroxide, said oxidizing agents in said oxidizing agents solution is ozone, wherein in the step (b), said temperature is 40° C., wherein in the step (c), said time is 5 minutes, wherein said yield of said final product of ferrate is 86~90%.

20. The method of synthesizing ferrate for producing ferrate composite pharmaceuticals according to claim 19, wherein a concentration of said oxidizing agents solution is 0.1 mol/L and said adding time is less than 0.5 minute, wherein said processing time for said method is approximately less than 30 minutes.

* * * * *